United States Patent [19]

van der Meer et al.

[11] Patent Number: 4,767,583

[45] Date of Patent: Aug. 30, 1988

[54] METHOD OF MANUFACTURING MOLDED BODIES FROM HYDROXYPHOSPHATE

[75] Inventors: Aant B. D. van der Meer; Petrus H. Swaanen, both of Eindhoven, Netherlands

[73] Assignee: U.S. Philips Corporation, New York, N.Y.

[21] Appl. No.: 876,046

[22] Filed: Jun. 19, 1986

[30] Foreign Application Priority Data

Jun. 27, 1985 [NL] Netherlands .......................... 8501848

[51] Int. Cl.$^4$ ............................................. C04B 35/64
[52] U.S. Cl. ....................................... 264/63; 264/65; 264/66
[58] Field of Search ............................. 264/63, 65, 66

[56] References Cited

U.S. PATENT DOCUMENTS 4,149,893  4/1979  Aoki et al. .......................... 501/123

FOREIGN PATENT DOCUMENTS 55-130854  10/1980  Japan .

OTHER PUBLICATIONS

Chemical Abstracts, vol. 94, 1981, p. 296, 179537w.
With et al, Preparation, Microstructure and Mechanical Properties of Dense Polycrystalline Hydroxy Apatite, in Journal of Materials Science, 16, 1981, pp. 1592–1598.

*Primary Examiner*—James Derrington
*Attorney, Agent, or Firm*—Norman N. Spain

[57] ABSTRACT

In dental surgery and orthopedic surgery, implants of the bio-compatible hydroxyphosphate are used. Molded bodies or a granulate thereof are obtained by sintering in a moist oxygen atmosphere. These products are of a blue color. In accordance with the invention, white products are obtained by sintering in an inert atmosphere in which the oxygen concentration is maximally 0.005%.

4 Claims, No Drawings

METHOD OF MANUFACTURING MOLDED BODIES FROM HYDROXYPHOSPHATE

BACKGROUND OF THE INVENTION

The invention relates to a method of manufacturing molded bodies or a granulate from calcium hydroxyphosphate and to the molded bodies and the granulate thus obtained.

Hydroxyphosphate is often used as an implantation body in dental surgery and orthopaedic surgery due to the fact that this compound exhibits an excellent biocompatibility. A granulate of this composition is used in plastic surgery as a filler, for example, for correcting facial asymmetry.

A method of manufacturing these bodies is known from an article by G. de With c.s. in J. Mat Sci 16 (1981) 1592-1598. In accordance with this method a powdered calcium hydroxyphosphate [$Ca_5(PO_4)_3OH$] is isostatically pressed to form a body which is sintered in a water-vapour containing oxygen atmosphere at a temperature of 1200°-1300° C.

However, the body thus obtained has a blue colour, probably caused by impurities present in the starting material.

However, there are disadvantages attached to the presence of a blue color, in particular, when the application of the material is readily visible, such as with dental protheses. However, also in the case of invisible application in the human or animal body there is a psychological objection to the blue color as shown very different from the color of the natural bone.

It is an object of the invention to provide molded bodies and a granulate of hydroxyphosphate having a white color.

It has been considered to obtain this color by rigorously purifying the raw materials or hot pressing the material at a much lower temperature than the sintering temperature, but at high pressure, but these possibilities had to be abandoned because of the complexity and high cost of these operations.

In accordance with Japanese Patent Application No. 80/130 854 which is laid open to public inspection and to which reference is made in Chemical Abstracts 94 (1981), 179 537W, a white color is obtained by sintering the starting materials at a temperature of 1100° C. or hot pressing at a temperature between 700° and 1200° C. in a flow of an inflammable gas mixture of H, CO, water-gas and/or cracked $NH_3$-gas comprising water-vapour having a dew point of 5° C. Heating in such an inflammable gas mixture is objectionable, however, due to the fire or explosion hazard.

SUMMARY OF THE INVENTION

In accordance with the invention, the sintering operation of the calcium hydroxyphosphate is carried out in an inert atmosphere in which free oxygen is present in a concentration of maximally 0.005% and having a moisture content which, dependent upon the selected sintering temperature, ranges from 1.66 to 72.6 mm Hg. It appeared that the moisture limits are critical for obtaining the white color.

Preferably, the inert atmosphere consists of nitrogen.

Surprisingly, it was found that this sintering method did not reduce the mechanical strength of the material with respect to the material sintered in oxygen. It is also a great technological advantage that sintering in a reducing, inflammable atmosphere can be avoided.

DETAILED DESCRIPTION OF THE INVENTION

In accordance with a further elaboration of the invention it appeared that products having a blue colour due to sintering in a water-vapour containing, oxygen containing atmosphere can be converted to white products by post-heating them in an inert atmosphere containing maximally 0.005% of free oxygen.

This is particularly important for the manufacture of porous moulded bodies. In this case a relatively large amount of organic material is added to the starting material, which organic material must be combusted before firing. If the firing operation were to be carried out directly in an inert atmosphere, the organic material would decompose thereby depositing carbon.

In accordance with this embodiment of the method in accordance with the invention, the shaped material, among which an organic binder has been dispersed, is first heated in an oxygen containing atmosphere until all organic matter is combusted and/or evaporated without leaving any residue before it is sintered at a temperature between 1200° and 1300° C. in an inert, moist atmosphere containing maximally 0.005% of free oxygen and having a moisture content which, dependent upon the selected sintering temperature, ranges from 1.66 to 72.6 mm Hg.

The invention will now be described in more detail with reference to three examples of embodiments.

EXAMPLE 1

Using approximately 7% by weight of tylose as a binding agent and approximately 5% by weight of butylstearate as a lubricant, calcium monohydroxyphosphate powder having a grain size smaller than approximately 0.5 $\mu$m was mixed with water to form an extrusible mass. Tubes having an outside diameter of 6 mm and an inside diameter of 2.6 mm were extruded from this mass, and after drying they were sintered for 4 hours at 1200° C. in a water-vapour containing nitrogen atmosphere having a moisture content of approximately 15 mm Hg and an oxygen content of 0.005%. The product thus obtained was of a white colour.

In dental surgery these tubes are used as substructures for a prothesis.

EXAMPLE 2

Using only water as a binder, calcium monohydroxyphosphate powder having a grain size smaller than approximately 0.5 $\mu$m was shaped into granules having a diameter between 0.7 and 1.7 mm. After drying the granulate was sintered for 4 hours at 1250° C. in a moist nitrogen atmosphere having a moisture content of approximately 15 mm Hg and an oxygen content of 0.005%.

EXAMPLE 3

For the manufacture of a porous body for use as a bone prothesis, a mass was formed comprising calcium monohydroxyphosphate powder having a grain size smaller than approximately 0.5 $\mu$m, approximately 20% by weight of semolina and 15% by weight of water. The resistant mass was molded in a mold and subsequently sintered for 4 hours at 1250° C. in moist air having a moisture content of approximately 15 mm Hg. The body obtained was porous without any visible residue, but still had a blue color.

Next, the body was sintered for 4 hours at 1250° C. in a moist nitrogen atmosphere having a moisture content of approximately 15 mm Hg and containing 0.005% of oxygen. After the sintering process the product had a white color.

When in the method of the above described examples the oxygen content of the sintering atmosphere is selected to be higher than 0.005% by weight, the color of the end product gradually changes to blue via greyish blue as the oxygen content becomes higher. At an oxygen content of 0.010% by weight the color is clearly blue. At an oxygen concentration below 0.005% by weight, the color of the end product obtained is always white.

We claim:

1. A method of manufacturing molded bodies of a granulate from calcium hydroxyphosphate by sintering a shaped starting material consisting essentially of a mixture of said phosphate and a dispersed organic bonder, in a water-vapor containing atmosphere at a temperature of between 1200° and 1300° C., characterized in that the sintering operation is carried out in an atmosphere consisting essentially of an inert gas in which free oxygen is present in a concentration of maximally 0.005%, and having a moisture content which, dependent upon the selected sintering temperature, ranges from 1.66 to 72.6 mm Hg.

2. A method as claimed in claim 1, characterized in that nitrogen is used as the inert atmosphere for the sintering operation.

3. A method of manufacturing porous moulded bodies from a shaped starting material as claimed in claim 1, characterized in that the shaped starting material, among which an organic binder has been dispersed, is first heated in an oxygen containing atmosphere until all of the organic matter is combusted and/or evaporated without leaving any residue, before it is sintered at a temperature between 1200° and 1300° C. in an inert water-vapour containing atmosphere having a moisture content which, dependent upon the selected sintering temperature, ranges from 1.66 to 72.6 mm Hg and in which maximally 0.005% of oxygen is present.

4. A method for the conversion of a white colored product from a blue colored product made by sintering, in a water-vapor and oxygen containing atmosphere compositions essentially consisting of calcium hydroxyphosphate, said method comprising resintering the resultant blue colored product at a temperature of between 1200° C. and 1300° C. in an atmosphere consisting essentially of an inert gas and containing maximally 0.005% of free oxygen and having a moisture content of from 1.66 to 12.6 mm Hg depending on the sintering temperature employed.

* * * * *